United States Patent

Naujokas et al.

[11] Patent Number: 5,747,547
[45] Date of Patent: May 5, 1998

[54] RECOVERY OF COMPONENTS FROM POLYESTER RESINS

[75] Inventors: Andrius Algimantas Naujokas, Webster; William James Gamble, Rochester, both of N.Y.

[73] Assignee: Eastman Kodak Company, Rochester, N.Y.

[21] Appl. No.: 687,883

[22] Filed: Jul. 26, 1996

Related U.S. Application Data

[60] Provisional application No. 60/002,163, Aug. 11, 1995.
[51] Int. Cl.⁶ ..................... C08J 11/04
[52] U.S. Cl. ............. 521/48.5; 521/48; 528/481; 528/496
[58] Field of Search ............... 521/48, 48.5; 528/481, 528/496

[56] References Cited

U.S. PATENT DOCUMENTS

| 3,907,868 | 9/1975 | Currie et al. | 260/475 |
| 5,414,022 | 5/1995 | Toot, Jr. et al. | 521/48 |
| 5,432,203 | 7/1995 | DeBruin et al. | 521/48 |
| 5,576,456 | 11/1996 | Gamble et al. | 528/481 |

*Primary Examiner*—Vasu Jagannathan
*Assistant Examiner*—Olga Asinovsky
*Attorney, Agent, or Firm*—Arthur H. Rosenstein

[57] ABSTRACT

There is described a process and apparatus for the depolymerization of polyester resins, such as polyethylene terephthalate into component monomers using a countercurrent or crossflow reactor.

6 Claims, 3 Drawing Sheets

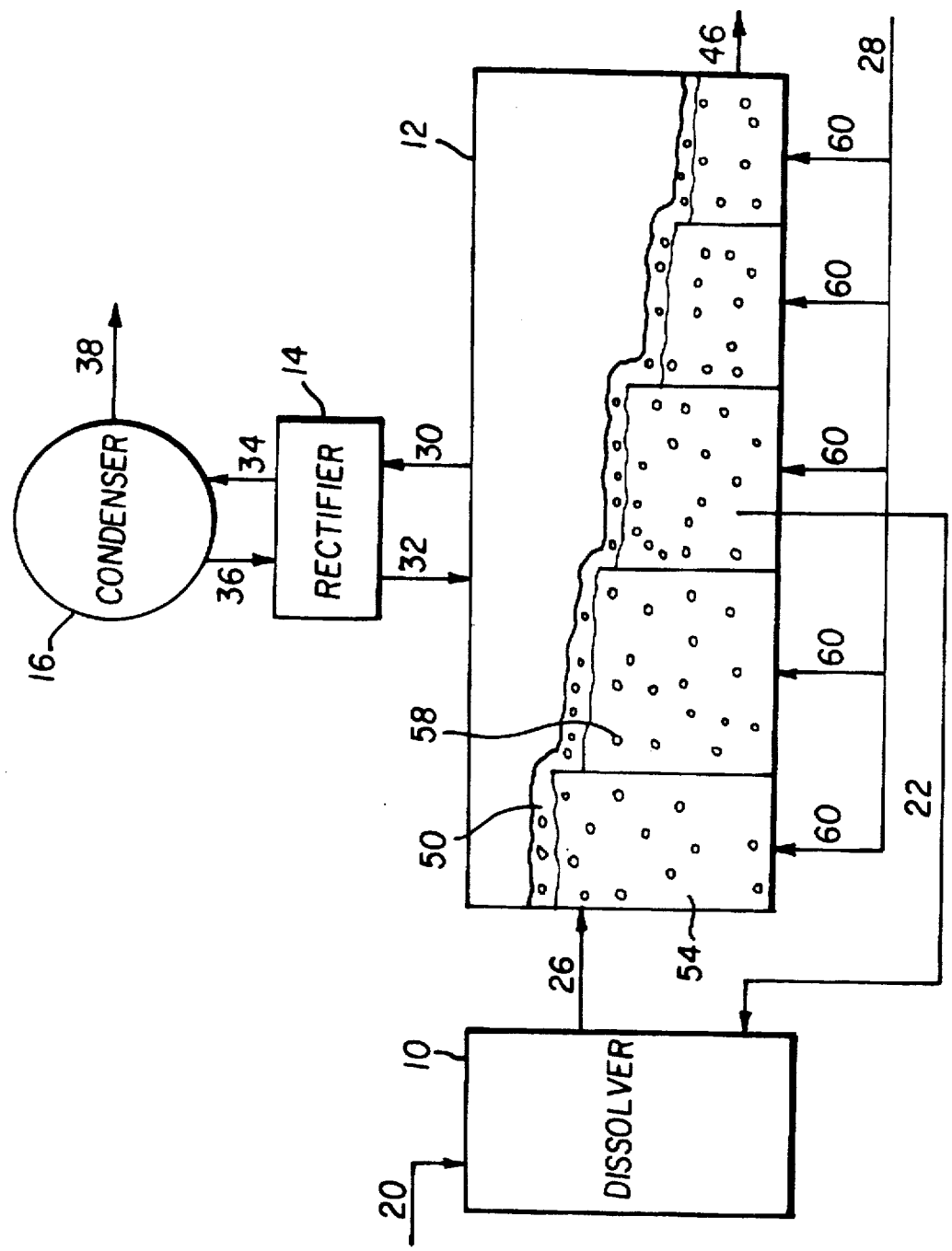

RECOVERY OF COMPONENTS FROM POLYESTER RESINS

CROSS REFERENCE TO RELATED APPLICATION

Reference is made to and priority claimed from U.S. Provisional application Ser. No. US 60/002,163, filed 11 Aug. 1995, entitled RECOVERY OF COMPONENTS FROM POLYESTER RESINS.

FIELD OF INVENTION

This invention relates to a process for recovery of ester and glycol components from condensation-type polyester resins and to apparatus for carrying out that process.

BACKGROUND OF THE INVENTION

Polyester resins have found widespread use in varied applications. Polyesters such as polyethylene terephthalate are used in photographic film, in magnetic tape, in fibers, and in food and beverage containers. Various methods have been disclosed for the depolymerization of such resins into their component monomers, such as ethylene glycol and terephthalic acid or derivatives thereof, so that they can be reused.

Some of these methods are described in such patents as U.S. Pat. Nos. 3,037,050, 3,321,510, 3,884,850, 3,907,868, 4,163,860, 4,578,502, 4,620,032, 4,876,378 and 5,095,145, and in European Published Patent Application 0 484 963 published May 13, 1992.

A particularly useful technique for recovering scrap polyester is described in a series of patents that begins with Naujokas et al. U.S. Pat. No. 5,051,528. This patent describes a process of recovering ethylene glycol and dimethyl terephthalate from polyethylene terephthalate scrap resins by dissolving the polyester resin in oligomers of the same monomers as are present in the polyester, passing super-heated methanol through the solution and recovering ethylene glycol and dimethyl terephthalate.

Gamble et al. U.S. Pat. No. 5,298,530, issued Mar. 29, 1994 improves on the process of the '528 patent by combining scrap resin with reactor melt in a dissolver before the dissolver melt is transferred to the reactor for contact with super-heated methanol. In the reactor, polymers and oligomers are further depolymerized into the component glycol and ester monomers, which are then recovered.

Toot et al. U.S. Pat. No. 5,414,022, issued May 9, 1995, optimizes the conditions of processes of Naujokas et al. and Gamble et al., cited above.

DeBruin et al U.S. Pat. No. 5,432,203, issued Jul. 11, 1995, extends the processes of prior patents in the series to convert ethylene glycol and dimethyl terephthalate to bishydroxyethyl terephthalate, which then can be used as feedstock for the formation of polyethylene terephthalate.

The processes described in this series of patents and applications have numerous advantages. These include low cost, high efficiency, the ability to operate at relatively low pressure and the ability to be used with a variety of forms of polyester of varying degrees of cleanliness and purity.

The processes and equipment described in this series of patents and applications employ a reactor in which a discontinuous phase of superheated methanol is passed through a continuous phase of molten polyester and polyester decomposition products. While such a reactor is useful, the apparatus must be shut down periodically to remove contaminants and impurities which collect in the system. In practice, contaminants can be carried into the system in the scrap feedstock. They can be components of the polyester being recovered or they can be non-polyester plastics that are introduced inadvertently. Further, side reactions and thermal degradation produces low volatility impurities as the process proceeds. The terms "contaminants" and "impurities" will be used interchangeably herein to describe unwanted materials in the reaction mixture, from whatever source derived.

As these impurities accumulate, phase separation occurs. The impurities that have densities similar to or heavier than the melt generally disperse in the melt, while lower density impurities form a layer on the melt surface. As they accumulate, the specific conversion rate of polyester to monomer tends to diminish due to dilution of the polyester oligomers. Eventually the reactor must be purged.

Purging generally is accomplished by stopping the feed of polyester scrap while continuing methanol flow. This step is continued until a significant amount of the polyester components are removed with the methanol. The residue then is removed from the reactor and the reactor restarted. These periodic cleanouts constitute an interruption of the steady state operation of the system. While there are other means of separating impurities, they require additional apparatus and are not as effective as periodic cleanout.

Thus, it would be desirable to have a reactor design which reduces the need for periodic cleanout and the concomitant interruption in the operation of the reactor.

We have devised apparatus and processes using a staged countercurrent or crossflow reactor which continuously removes contaminants and impurities from the reactor, thus reducing the need for periodic cleanouts.

SUMMARY OF THE INVENTION

The present invention provides a process for converting polyester to its component monomers. The apparatus used to carry out the process of the present invention is similar to that used in the process described in U.S. Pat. No. 5,298,530. One significant difference is that the reactor in which the bulk of the depolymerization reaction takes place is a staged countercurrent or crossflow reactor.

The present invention provides a process for depolymerizing polyester into its components using apparatus that comprises:

a dissolver for receiving polyester and a staged countercurrent or crossflow reactor for depolymerizing polyester into monomer components and for separating monomer components from lower density and higher boiling impurities, the process comprises the steps of:

a) forming a melt of polyester in the dissolver;

b) transferring polyester from the dissolver to the reactor so that the melt flows through the stages of the reactor from an entry point to an exit point;

c) introducing super-heated methanol into the reactor so that methanol travels through the reactor;

d) causing the methanol to contact the melt to depolymerize polyester into component monomers;

e) continuously removing component monomers and methanol from the reactor as a vapor phase; while f) continuously removing impurities and contaminants from the reactor at the exit point.

In the embodiment where the reactor is a countercurrent reactor, the methanol and melt travel through the reactor in directions substantially counter to one another, the melt entering the reactor in the region where the methanol exits and exiting the reactor in the region where the methanol enters. The methanol vapor stream exiting the reactor takes with it the desired vapor phase reaction products. The reaction conditions can be adjusted so that the melt exiting the reactor essentially is a waste stream of impurities and undesired reaction by-products.

In the embodiment where the reactor is a crossflow reactor, the methanol and melt travel through the reactor in directions substantially perpendicular to one another. As in the case of the countercurrent reactor, the methanol vapor stream exiting the reactor takes with it the desired vapor phase reaction products while the melt exiting the reactor can be a waste stream of impurities and undesired reaction by-products.

In a preferred embodiment, the polyester melt added to the dissolver is combined with melt withdrawn from the reactor, and the two are retained in the dissolver for a period of time sufficient to initiate depolymerization of the polyester and provide reduced chain length polyester for use as the melt which is introduced into the reactor.

The present invention provides a process, and apparatus for performing it, that permits recovery of component monomers from polyester in an efficient manner while minimizing the need to shut down the reactor for cleaning.

BRIEF DESCRIPTION OF THE DRAWINGS

FIGS. 4 is a schematic diagram illustrating apparatus of this invention that utilize a staged crossflow reactor.

DETAILED DESCRIPTION OF THE INVENTION

The two staged reactors utilize the same principle. The melt of polyester oligomer enters a feed stage in the reactor and travels toward an exit stage. Light phase impurities are carried on the top of the melt and flow toward the reactor exit for continuous removal with the waste residue of the depolymerization reaction. Separation of the reactor stages is accomplished using downcommers and bubble trays in the countercurrent reactor and weirs in the crossflow reactor. The heavy impurities are maintained in suspension in the melt by agitation provided by the methanol vapor moving through the melt. The heavy impurities flow toward the reactor exit with the melt and are removed from the reactor together with the light phase impurities and other waste.

In a countercurrent reactor, super heated methanol vapor enters the reactor in the region where the impurities exit. In a crossflow reactor super heated methanol vapor is introduced at the bottom of each stage. In either case, methanol vapor moves through the melt, causing depolymerization of polyester into its component monomers. The monomers are carried out of the reactor with the methanol vapor.

The number of stages and the operating conditions of the reactor will determine the composition of the waste residue, including the amount of polyester oligomer contained in it. The reactor residence time and composition can be adjusted to obtain an essentially polyester-free waste stream.

Lower viscosity liquid, such as high boiling glycols from associated recovery operations, can be added to the later stages of the reactor to reduce the viscosity of the waste and facilitate its discharge.

A benefit of these reactors is that the melt does not backmix. This improves the driving force of the depolymerization reaction.

Figure 1:
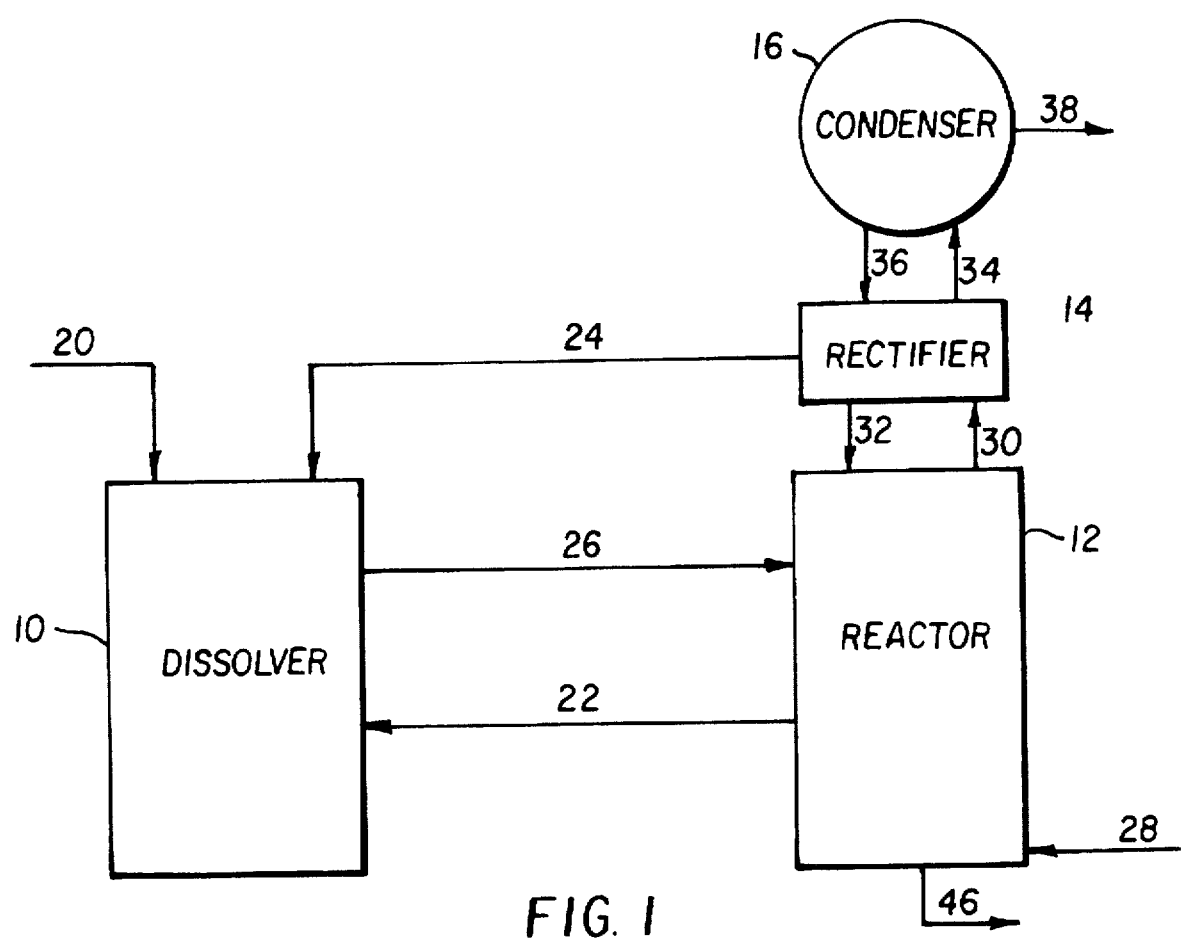
FIG. 1 is a schematic diagram illustrating preferred apparatus in which the process of this invention can be carried out.

The process and apparatus used in this invention, except for the reactor details, are similar to that described in detail in the Naujokas et al, Gamble et al. and Toot et al. patents referred to above, the disclosures of which are incorporated herein by reference. In this apparatus, as shown in FIG. 1 a dissolver (10), a reactor (12), a rectifier (14), and a condenser (16) are connected to transfer materials from one location to another in accordance with the reaction.

In practice, polyethylene terephthalate (20) in a suitable form and size is introduced into the dissolver by any suitable means where it is liquefied and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

One or both of melt (22) from the reactor and liquid (24) from the rectifier can be introduced into the dissolver via suitable piping. Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst, such as zinc acetate. Such catalysts are known in the art to facilitate the depolymerization process.

The reactor melt and dissolver melt comprise methanol, low molecular weight polyesters, monomers, monohydric alcohol-ended oligomers, glycols, dimethyl terephthalate and methylhydroxyethyl terephthalate. The major difference between these two melts is the average chain length of the polyester. The rectifier liquid contains the same components except for polyesters.

The viscosity of the dissolver melt preferably is maintained in the range of 0.002 to 0.1 Pa.s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The gases which evolve in the dissolver contain monomers that preferably are recovered together with the monomers exiting the reactor. This can be accomplished by passing the gases to a scrubber (not shown) where they are treated with and absorbed by liquid methanol. This material can then be passed to recovery apparatus where it can be combined with the vapor stream exiting the rectifier for recovery.

Melt (26) from the dissolver is transferred to the reactor where it is contacted with superheated methanol vapor (28) as described below in connection with FIGS. 2, 3 and 4.

There is transferred from the reactor to the rectifier a vapor stream (30) comprising methanol, dimethyl terephthalate, glycols including ethylene glycol, diethylene glycol, and triethylene glycol, dimethyl isophthalate, cyclohexanedimethanol, and methylhydroxyethyl terephthalate. The rectifier separates the higher boiling components, such as methylhydroxyethyl terephthalate and esterification catalyst from the vapor stream exiting the reactor. They can be routed to the dissolver in the form of a liquid together with dimethyl terephthalate, glycols and methanol or all or portion (32) can be returned to the reactor as a liquid.

The remainder of the vapor stream (34) is transferred from the rectifier to a condenser (16) where part of the condensed liquid (36) is returned to the rectifier and the product stream (38) is sent for recovery. The condenser provides reflux to the column and can be adjusted to control the temperature profile in the column.

Figure 2:
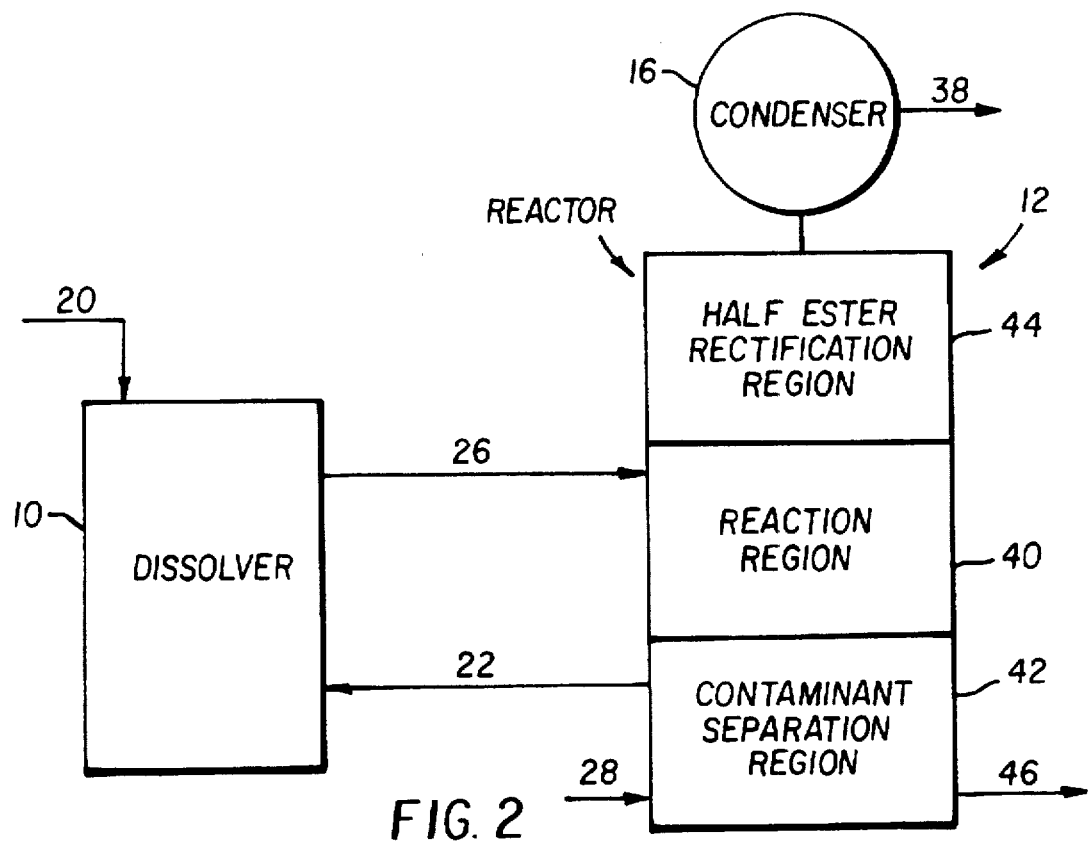
FIG. 2 is a schematic diagram illustrating apparatus of this invention that utilizes a staged countercurrent reactor.

The countercurrent reactor shown in FIG. 2 is similar to a fractionating column or a stripping column in design. It comprises:

1. An appropriate number of stages that use bubble cap, sieve tray, valve tray, or similar function to allow methanol vapor to flow up the column and contact the melt, so as to effect depolymerization.

2. Downcommers to allow liquid melt to overflow into the stage below.

3. A heater to maintain the column at the desired reaction temperature.

4. A discharge for the waste stream from the last stage.

FIG. 2 shows a continuous countercurrent reactor (12) containing a number of stages which can conceptually be divided into a reaction region (40), a contaminant separation region (42) and a half ester rectification region (44). This reactor design avoids the need for a separate rectifier (14) shown in FIG. 1. Alternatively, separate staged columns can be used to perform these three operations.

Solid polyester scrap (20) is melted, and optionally reduced in molecular weight, in the dissolver (10). Reduction in molecular weight can be accomplished by recycling a portion of the low molecular weight oligomer melt (22) from the reactor to the dissolver. This step reduces the viscosity of the feed for easier pumping. The melt (26) enters the reactor in the reaction region (40) where it contacts methanol (28) and reaction products carried with the methanol from lower stages. The melt travels down the column where additional depolymerization occurs and the contaminant level increases. In the bottom stages (42), residual polyester oligomer and the impurities and contaminants in the waste stream (46) are removed.

The reaction products, dimethyl terephthalate, ethylene glycol, and methylhydroxyethyl terephthalate, are carried up the column as a gas phase where they contact the liquid phase in stages above. In the upper stages (44), rectification takes place and the half ester, methylhydroxyethyl terephthalate, is returned to lower stages to complete the depolymerization reaction.

FIG. 2 shows methanol vapor (28) addition in the bottom stage. Optionally, methanol can be also added in upper stages.

Figure 3:
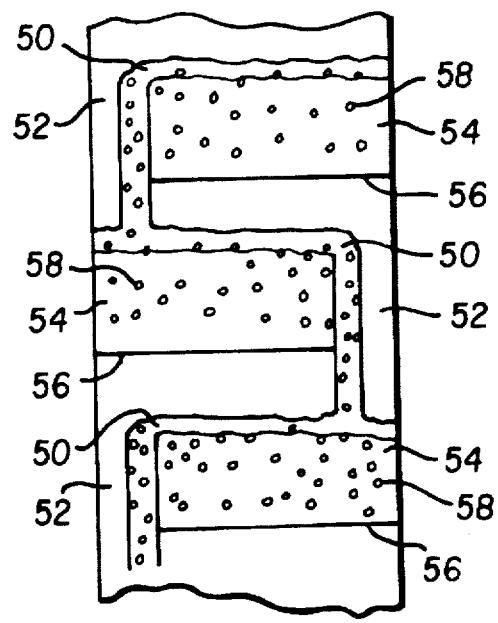
FIG. 3 is a detail of several stages of the reactor of FIG. 1.

FIG. 3 is a detail of several stages of the reactor of FIG. 2, and shows how the immiscible light layer (50) will travel to the bottom of the column. Since the light layer floats on the melt, it will overflow the lips of the downcommers (52) and be transported to the stage below. Likewise, dispersed fine solids and dissolved low volatility contaminants will be transported with the oligomer melt (54) to the stage below via the downcommers. Methanol vapor and vapor phase reaction products (58) rise through the melt and pass from stage to stage through bubble trays (56) or similar apparatus.

FIG. 4 shows a continuous crossflow reactor (12). As in the case of FIG. 2, solid scrap can be reduced in molecular weight in a dissolver (10) by addition of low molecular weight oligomers (22) from one of the reactor stages. The feed (26) is pumped into the first stage (the feed stage) of the reactor where it is mixed with melt (54) already present in that stage. Each of the stages has a means (60), such as a sparger, to distribute methanol vapor (28). The reactor is constructed so that subsequent stages are at progressively lower levels than the feed stage. Thus, the light immiscible impurities (50) will accumulate on the melt surface and will overflow into the next lower stage. As melt (54) travels through the stages, depolymerization products (58) are removed with the methanol vapor and transported to the rectifier (14). This causes the contaminants to concentrate in the later stages. As indicated above, lower viscosity liquids, such higher glycols from separate purification operations, can be added to later stages to adjust the viscosity of the waste stream (46).

The rate of addition of scrap and the methanol vapor flow in each stage can be adjusted to optimize the reactor operation. The construction of this reactor allows for elimination of the dissolver, if desired. In such a design polyester scrap is added directly to the fist stage of the reactor where it will melt and dissolve in the reactor melt already present.

The staged continuous reactors used in this invention can be arranged in a number of different ways. For instance, combinations of two or more countercurrent and crossflow reactors can be grouped in a reactor train. The volumes of the stages can be designed to obtain the required residence times for optimum reactor operation.

The invention has been described by reference to preferred embodiments, but it will be understood changes can be made to the apparatus and process steps specifically described herein within the spirit and scope of the invention.

What is claimed is:

1. A process for depolymerizing polyester into its components the process comprising the steps of:

a) forming a melt of polyester in the dissolver;

b) transferring polyester from the dissolver to a reactor so that the melt flows through stages of the reactor from an entry point to an exit point;

c) introducing super-heated methanol into the reactor so that methanol travels through the reactor at either a countercurrent or crossflow direction to said polyester in the reactor;

d) causing methanol to contact the melt to depolymerize polyester into component monomers;

e) continuously removing component monomers and methanol from the reactor as a vapor phase; while f) continuously removing impurities and contaminants from the reactor at the exit point.

2. A process of claim 1, wherein the reactor is a countercurrent reactor and the methanol and melt travel through the reactor in directions substantially counter to one another, the melt entering the reactor in the region where the methanol exits and exiting the reactor in the region where the methanol enters.

3. A process of claim 1 wherein the reactor is a crossflow reactor, the methanol and melt travel through the reactor in directions substantially perpendicular to one another.

4. A process of claim 1, wherein the polyester added to the dissolver is combined with melt withdrawn from the reactor and the two are retained in the dissolver for a period of time sufficient to initiate depolymerization of the polyester and provide reduced chain length polyester for transfer to the reactor.

5. A process of claim 3, wherein the the dissolver is the first stage of the reactor, scrap polyester being added directly thereto.

6. A process of claim 1, wherein lower viscosity liquids are added to later stages of the reactor to reduce the viscosity of the melt in those stages.

* * * * *